US00PP29286P3

(12) United States Plant Patent
Klemm et al.

(10) Patent No.: US PP29,286 P3
(45) Date of Patent: May 8, 2018

(54) ***SUTERA* PLANT NAMED 'KLESG15004'**

(50) Latin Name: *Sutera grandiflora*
Varietal Denomination: KLESG15004

(71) Applicant: Klemm+Sohn GmbH & Co. KG, Stuttgart (DE)

(72) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 140 days.

(21) Appl. No.: 15/330,042

(22) Filed: Jul. 28, 2016

(65) Prior Publication Data

US 2017/0295711 P1 Oct. 12, 2017

Related U.S. Application Data

(60) Provisional application No. 62/390,712, filed on Apr. 6, 2016.

(51) Int. Cl.
*A01H 5/02* (2018.01)

(52) U.S. Cl.
USPC ..... Plt./485
CPC ..... *A01H 5/02* (2013.01)

(58) Field of Classification Search
USPC ..... Plt./485
See application file for complete search history.

*Primary Examiner* — Anne Marie Grunberg
(74) *Attorney, Agent, or Firm* — James M. Weatherly; Bethany R. Roahrig; Cochran Freund & Young LLC

(57) ABSTRACT

A new *Sutera* plant particularly distinguished by having large flowers with a light blue flower color, good quality and very good branching, is disclosed.

1 Drawing Sheet

Genus and species: *Sutera grandiflora*.
Variety denomination: 'KLESG15004'.

BACKGROUND OF THE NEW PLANT

The present invention comprises a new and distinct variety of *Sutera*, botanically known as *Sutera grandiflora*, and hereinafter referred to by the variety name 'KLESG15004'. 'KLESG15004' originated from an open-pollination in the summer of 2011 in Stuttgart, Germany, between the proprietary female *Sutera* variety 'SG-2011-0073' (unpatented) and an unknown male *Sutera* variety.

In August of 2011, seed was collected from the open-pollination cross of two *Sutera* parental lines, 'SG-2011-0073' and an unknown *Sutera* in Stuttgart, Germany. The seeds were sown in February 2012 and plants were grown for evaluation. A plant line was selected in May 2012 and subsequently named 'KLESG15004'. In May 2012, 'KLESG15004' was first vegetatively propagated by in-vitro cultivation in Stuttgart, Germany and in Italy. 'KLESG15004' was found to reproduce true to type in successive generations of asexual propagation via in-vitro cultivation.

SUMMARY

The following are the most outstanding and distinguishing characteristics of this new variety when grown under normal horticultural practices in Stuttgart, Germany.

1. Large flowers with a light blue flower color;
2. Good flower quality; and
3. Very good branching.

DESCRIPTION OF THE PHOTOGRAPH

This new *Sutera* plant is illustrated by the accompanying photograph, which shows an overall view of the plant. The photograph is of a 13-week-old plant grown in Stuttgart, Germany in July of 2013.

The colors shown are as true as can be reasonably obtained by conventional photographic procedures.

DESCRIPTION OF THE NEW VARIETY

The following detailed descriptions set forth the distinctive characteristics of 'KLESG15004'. The data which define these characteristics were collected from asexual reproductions carried out in Stuttgart, Germany. Data was collected on 10-week-old plants after potting, grown in a controlled greenhouse environment in Stuttgart, Germany in June of 2016. Color references are to The R.H.S. Colour Chart of The Royal Horticultural Society of London (R.H.S.), 5$^{th}$ edition (2005).

Classification:
- *Family*.—Scrophulariaceae.
- *Botanical*.—*Sutera grandiflora*.
- *Common*.—*Sutera*.
- *Designation*.—'KLESG15004'.

Parentage:
- *Female parent*.—Proprietary *Sutera* line 'SG-2011-0073' (unpatented).
- *Male parent*.—An unknown *Sutera* line.

Plant:
- *Habit*.—Trailing, flat.
- *Height*.—3.0 cm to 5.0 cm.
- *Spread*.—40.0 cm.
- *Life cycle*.—Blooms from spring until September.
- *Form*.—Trailing, round.
- *Time to produce a rooted cutting*.—Four weeks.
- *Time to bloom from propagation*.—First flowers could be observed after 3 weeks. Finished product is after 9 to 10 weeks.
- *Lastingness of inflorescence on the plant*.—About 7 days.
- *Rooting habit*.—Fine, fibrous roots.
- *Root color*.—White to cream white.

Stems:

*Number of stems per plant.*—5.

*Length.*—26.0 cm.

*Diameter.*—0.3 cm.

*Internode length.*—About 2.5 cm.

*Color.*—RHS 138A.

*Texture.*—Smooth.

*Anthocyanin.*—Absent.

Leaves:

*Arrangement.*—Single, opposite.

*Type.*—Simple.

*Number of leaves per branch.*—About 30, depends on the age of the plant.

*Variegation.*—Absent.

*Shape.*—Ovate, acute angle to the stem.

*Apex.*—Acute.

*Base.*—Cordate.

*Margin.*—Serrate.

*Length.*—2.2 cm.

*Width.*—2.0 cm.

*Color.*—Immature leaf: Upper surface: RHS 138A. Lower surface: RHS 138D. Mature leaf: Upper surface: RHS N137C. Lower surface: RHS 138A.

*Texture.*—Upper surface: Leathery. Lower surface: Leathery.

*Venation type.*—Pinnate.

*Venation color.*—Upper surface: RHS N137C. Lower surface: RHS 138A.

*Petiole.*—Length: 0.7 cm. Diameter: 0.2 cm. Texture: Smooth. Color: RHS N137A.

Inflorescence:

*Blooming habit.*—Freely flowering.

*Quantity of inflorescence per stem.*—About 12.

*Type of inflorescence.*—Flowers are often solitary, most often 2 flowers per node are developed, persistent.

*Natural flowering season.*—Spring until September.

*Fragrance.*—Flower is not fragrant, but foliage has the typical *Sutera* fragrance.

*Pedicel.*—Color: RHS 138A. Length: About 1.0 cm. Diameter: 0.1 cm. Texture: Pubescent. Strength: Moderate.

*Peduncle.*—Length: 6.0 cm to 10.0 cm. Diameter: 0.3 cm. Color: RHS 137D. Texture: Pubescent. Strength: Moderate.

*Corolla (flower).*—Bud: Shape: Tubular. Diameter: 0.4 cm. Length: 0.6 cm. Color (at tight bud): RHS 157A (by maturing it changes to RHS 112D).

*Type and shape.*—Single-type, nearly round, lower part tube and funnel shaped formed by 5 fused petals, upper part is salver shaped formed by the partly free petal lobes.

*Corolla, horizontal diameter.*—2.2 cm.

*Corolla, total length.*—0.5 cm. Color of throat: Inner surface: RHS 23A. Outer surface: RHS 23C.

*Funnel/tube.*—Length: 0.5 cm. Diameter: 0.4 cm. Texture of funnel: Inner surface: Smooth. Outer surface: Smooth.

*Petal (lobes).*—Length: 0.9 cm. Width: 0.7 cm. Apex: Rounded tips. Base: Fused. Margin: Entire. Color: Inner surface: RHS 91D. Outer surface: RHS 91C. Texture: Upper surface: Smooth. Lower surface: Smooth.

*Calyx.*—Arrangement and appearance: Whorl of 5 sepals surrounding the base of the flower tube, sepals are fused at the base. Sepals: Color: Upper surface: RHS 137D. Lower surface: RHS 137D. Length: 0.6 cm. Width: 0.1 cm. Shape: Apex: Acute. Base: Fused. Margin: Entire. Texture: Upper and lower surfaces: Densely pubescent.

Reproductive organs:

*Stamens.*—Quantity: 4. Filament: Color: RHS 155B. Length: 0.5 cm. Diameter: 0.1 cm. Anther color: RHS 23A. Pollen amount: Abundant. Pollen color: RHS 23A.

*Pistil.*—Quantity per flower: 1. Length: 1.3 cm. Stigma color: RHS 145C. Style color: RHS 145D. Style length: 0.8 cm. Ovary color: RHS 145D.

Fruit and seed set: None observed.

Disease and pest/insect resistance: None observed.

COMPARISON WITH PARENTAL LINE AND KNOWN VARIETY

'KLESG15004' is distinguished from its female parent as described in Table 1:

TABLE 1

Comparison with Parental Line

| Trait | Variety 'KLESG15004' | Female parent 'SG-2011-0073' |
|---|---|---|
| Flower color | Light blue | Lavender |
| Branching | Very good | Bad |

'KLESG15004' is most similar to the *Sutera* plant named 'KLESG14831' (U.S. Plant Pat. No. 27,738). Differences between the two varieties are described in Table 2:

TABLE 2

Comparison with Similar Variety

| Trait | Variety 'KLESG15004' | Commercial line 'KLESG14831' |
|---|---|---|
| Flower color | Light Blue | Blue |

We claim:

1. A new and distinct variety of *Sutera* plant named 'KLESG15004' as illustrated and described herein.

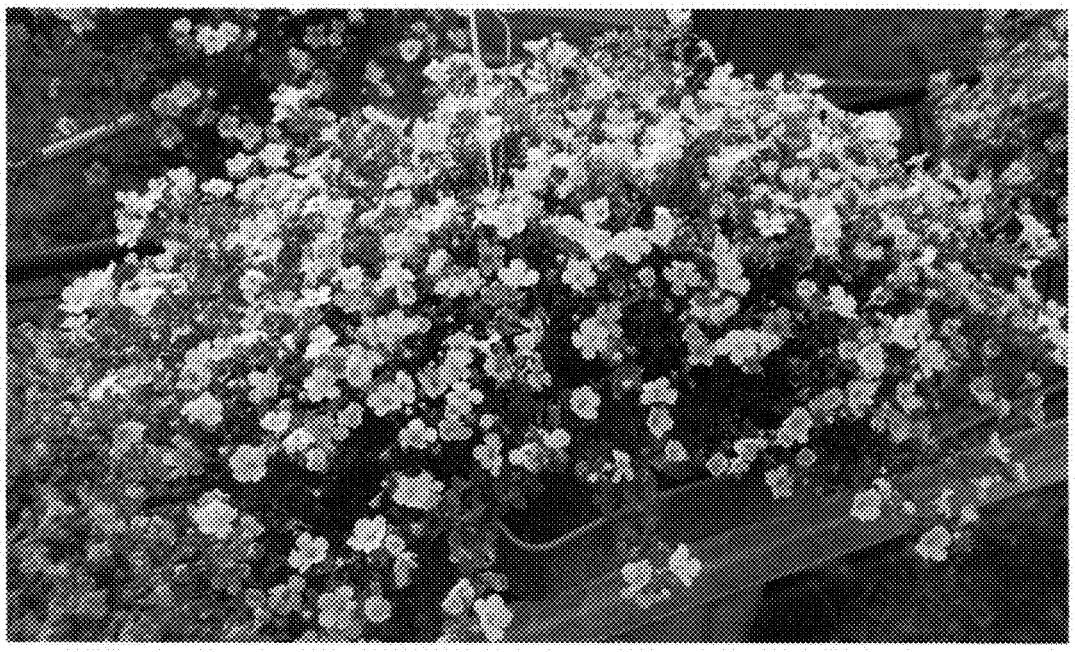

* * * * *